US011045105B2

(12) United States Patent
Hallbäck

(10) Patent No.: US 11,045,105 B2
(45) Date of Patent: Jun. 29, 2021

(54) DETERMINATION OF CARDIAC OUTPUT OR EFFECTIVE PULMONARY BLOOD FLOW DURING MECHANICAL VENTILATION

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 202 days.

(21) Appl. No.: 16/098,080

(22) PCT Filed: May 3, 2016

(86) PCT No.: PCT/SE2016/050402
§ 371 (c)(1),
(2) Date: Oct. 31, 2018

(87) PCT Pub. No.: WO2017/192076
PCT Pub. Date: Nov. 9, 2017

(65) Prior Publication Data
US 2019/0142284 A1    May 16, 2019

(51) Int. Cl.
*A61B 5/02* (2006.01)
*A61B 5/029* (2006.01)
(Continued)

(52) U.S. Cl.
CPC .............. *A61B 5/029* (2013.01); *A61B 5/021* (2013.01); *A61B 5/0205* (2013.01); *A61B 5/08* (2013.01);
(Continued)

(58) Field of Classification Search
CPC ....... A61B 5/029; A61B 5/0205; A61B 5/021; A61B 5/08; A61B 5/0836; A61B 5/4836;
(Continued)

(56) References Cited

U.S. PATENT DOCUMENTS 4,877,035 A * 10/1989 Bogen .................. A61B 5/0215
600/486
5,178,151 A * 1/1993 Sackner ............... A61B 5/1135
600/485

(Continued)

FOREIGN PATENT DOCUMENTS

CN    103315730    5/2002
CN    104323765    2/2015
(Continued)

OTHER PUBLICATIONS

Peyton et al, "*Noninvasive, automated and continuous cardiac output monitoring by pulmonary capnodynamics: breath-by-breath comparison with ultrasonic flow probe*", Anesthesiology, Jul. 1, 2006, pp. 72-80.

(Continued)

*Primary Examiner* — Carl H Layno
*Assistant Examiner* — Michael J Lau
(74) *Attorney, Agent, or Firm* — Fay Kaplun & Marcin, LLP

(57) ABSTRACT

The present disclosure relates to a method for determination of cardiac output or EPBF of a mechanically ventilated subject. The method comprises the steps of introducing a change in the effective ventilation of the subject, measuring expiratory flow and CO2 during a sequence of analyzed breaths during which the effective ventilation of the subject varies, and determining the cardiac output or EPBF of the subject using the flow and CO2 measurements. The method further comprises the steps of measuring also a relative variation in cardiac output or EPBF during the sequence of analyzed breaths, and using the relative variation in the determination of cardiac output or EPBF.

13 Claims, 2 Drawing Sheets

(51) Int. Cl.
  *A61B 5/021*  (2006.01)
  *A61B 5/083*  (2006.01)
  *A61B 5/00*  (2006.01)
  *A61B 5/08*  (2006.01)
  *A61M 16/00*  (2006.01)
  *A61B 5/0205*  (2006.01)
  *A61B 5/024*  (2006.01)

(52) U.S. Cl.
  CPC .......... *A61B 5/0836* (2013.01); *A61B 5/4836* (2013.01); *A61B 5/4884* (2013.01); *A61B 5/7225* (2013.01); *A61B 5/746* (2013.01); *A61M 16/024* (2017.08); *A61B 5/024* (2013.01)

(58) Field of Classification Search
  CPC ..... A61B 5/4884; A61B 5/7225; A61B 5/746; A61B 5/024; A61M 16/024
  USPC ........................................................ 600/526
  See application file for complete search history.

(56) References Cited

U.S. PATENT DOCUMENTS

| | | | |
|---|---|---|---|
| 5,429,123 A * | 7/1995 | Shaffer | A61M 16/024 128/204.21 |
| 6,217,524 B1 | 4/2001 | Orr et al. | |
| 6,238,349 B1 * | 5/2001 | Hickey | A61B 5/0215 600/486 |
| 6,758,822 B2 | 7/2004 | Romano | |
| 7,135,001 B2 * | 11/2006 | Orr | A61B 5/029 600/526 |
| 7,740,591 B1 * | 6/2010 | Starr | A61B 5/0205 600/534 |
| 7,761,141 B2 * | 7/2010 | Hirsh | A61B 5/352 600/513 |
| 10,085,673 B2 | 10/2018 | Emtell et al. | |
| 2002/0198521 A1 * | 12/2002 | Maguire | A61N 7/02 606/41 |
| 2006/0155206 A1 * | 7/2006 | Lynn | A61B 5/412 600/529 |
| 2007/0118180 A1 * | 5/2007 | Ni | A61B 5/366 607/17 |
| 2007/0173728 A1 * | 7/2007 | Pu | A61B 5/02405 600/484 |
| 2007/0179386 A1 * | 8/2007 | Michard | A61B 5/0816 600/485 |
| 2008/0033305 A1 * | 2/2008 | Hatib | A61B 5/0285 600/485 |
| 2009/0048527 A1 * | 2/2009 | Hatib | A61B 5/02108 600/508 |
| 2010/0049184 A1 * | 2/2010 | George | A61B 18/02 606/21 |
| 2010/0280397 A1 * | 11/2010 | Feldman | A61B 5/204 600/486 |
| 2011/0077474 A1 * | 3/2011 | Huiku | A61B 5/4875 600/301 |
| 2011/0190751 A1 * | 8/2011 | Ingle | A61B 18/02 606/21 |
| 2011/0257549 A1 * | 10/2011 | Wysocki | A61M 16/024 600/529 |
| 2011/0270111 A1 * | 11/2011 | Cannesson | A61B 5/4869 600/521 |
| 2013/0253359 A1 * | 9/2013 | Emtell | A61M 16/0051 600/532 |
| 2014/0039333 A1 * | 2/2014 | Min | A61B 5/349 600/510 |
| 2014/0066732 A1 * | 3/2014 | Addison | A61B 5/029 600/324 |
| 2014/0073889 A1 * | 3/2014 | Su | A61M 16/0051 600/324 |
| 2014/0073890 A1 * | 3/2014 | Su | A61B 5/1455 600/324 |
| 2014/0296677 A1 * | 10/2014 | McEowen | A61B 5/0215 600/366 |

FOREIGN PATENT DOCUMENTS

| | | | | |
|---|---|---|---|---|
| EP | 2 799 008 | | 11/2014 | |
| WO | 2006/119546 | | 11/2006 | |
| WO | WO-2006119546 A1 * | | 11/2006 | ............ A61B 5/029 |
| WO | 2013/141766 | | 9/2013 | |
| WO | 2016/032375 | | 3/2016 | |
| WO | 2017/105304 | | 6/2017 | |

OTHER PUBLICATIONS

Peyton,"*Continuous minimally invasive peri-operative monitoring of cardiac output by pulmonary capnotracking: comparison with thermodilution and transesophageal echocardiography*", Journal of Clinical Monitoring and Computing, Kluwer, Academic Publishers, vol. 26, No. 2, Feb. 18, 2012, pp. 121-132.

* cited by examiner

DETERMINATION OF CARDIAC OUTPUT OR EFFECTIVE PULMONARY BLOOD FLOW DURING MECHANICAL VENTILATION

TECHNICAL FIELD

The present disclosure relates to a method, a computer program and a system for determination of cardiac output or effective pulmonary blood flow of a mechanically ventilated subject.

BACKGROUND

Monitoring of cardiac output and EPBF (effective pulmonary blood flow) is important when the cardiovascular stability of a subject is potentially threatened, e.g. during surgery or in critically ill patients. Therefore, it is often desired to monitor the cardiac output and/or the EPBF of mechanically ventilated patients.

Most non-invasive respiratory based methods for determination of cardiac output or EPBF are based on some form of the basic physiological principle known as the Fick principle. According to the Fick equation, the cardiac output of a patient may be determined using the following basic relationship:

$$Q = \frac{VCO2}{(CvCO2 - CaCO2)} \quad \text{Eq. 1}$$

where Q is cardiac output, VCO2 is the volume of carbon dioxide excreted from the body of a patient during respiration (carbon dioxide elimination), CvCO2 is the carbon dioxide concentration in venous blood of the patient, and CaCO2 is the carbon dioxide concentration in arterial blood of the patient.

As well known in the art, EPBF is directly derivable from the cardiac output as:

$$Q \cdot (1 - fs) = EPBF \quad \text{Eq. 2}$$

where fs is the pulmonary shunt fraction.

Most methods for cardiac output or EPBF determination employ differential Fick techniques based on the premise that cardiac output and EPBF can be estimated from measurable changes in CO2 elimination (VCO2) and partial pressure of CO2 of expired alveolar gas (PACO2). The measurable changes in VCO2 are normally introduced by changing the effective ventilation of the patient, meaning that the cardiac output or the EPBF of the mechanically ventilated subject is determined from an analysed sequence of breaths during which the effective ventilation of the patient is changed to cause a change in VCO2. The calculations for determination of cardiac output or EPBF and the ventilation pattern employed to cause the change in VCO2 may vary. Examples of calculations and ventilation patterns employed in prior art are described in e.g. WO 2006/119546, U.S. Pat. No. 7,135,001, WO2013/141766, EP2799008 and PCT/SE2015/051357.

One problem associated with these methods is that they are based on the assumption that the perfusion of the mechanically ventilated patient is constant during the analysed sequence of breaths, i.e. the sequence of breaths during which the flow and CO2 measurements used for cardiac output or EPBF determination are obtained. This assumption is often incorrect since the perfusion depends in part on the pressure in the thorax cavity, which in turn varies with the airway pressure of the patient. For example, in cases where the change in effective ventilation of the patient is effectuated by varying the duration of the expiratory phase of the breaths delivered to the patient by the ventilator, e.g. by varying the duration of the expiratory pause, the airway pressure during breaths of prolonged expiration is often somewhat lower than the airway pressure during breaths having shorter expiration phases. Therefore, the perfusion may be higher for breaths of prolonged expiration compared to breaths having shorter expiration phases. This increase in perfusion typically causes an increase in the level of CO2 in the lungs of the patient, which increase is not accounted for in the calculations of the cardiac output or EPBF, and so introduces a substantial error in the determination of cardiac output or EPBF.

Consequently, there is a need for a more precise method for cardiac output or EPBF determination.

SUMMARY OF THE DISCLOSURE

The present disclosure relates to improved determination of the cardiac output or EBPF of a mechanically ventilated subject.

In particular, the present disclosure relates to improvements within the field of respiratory based determination of the cardiac output or EPBF of mechanically ventilated subjects.

According to the present disclosure, a method for determination of cardiac output or EPBF of a mechanically ventilated subject, comprising the steps of introducing a change in the effective ventilation of the subject, measuring expiratory flow and CO2 during a sequence of analysed breaths during which the effective ventilation of the subject varies, and determining the cardiac output or EPBF of the subject using the flow and CO2 measurements. The method further comprises the steps of measuring also a relative variation in cardiac output or EPBF during the sequence of analysed breaths, and using the relative variation in the determination of cardiac output or EPBF.

By taking into account relative variations in the cardiac output or EPBF during the sequence of analysed breaths, the accuracy in the determination of (absolute) cardiac output or EPBF from measured flow and CO2 content can be increased.

As mentioned above, respiratory based determination of cardiac output or EPBF, e.g. by means of a Fick based technique, requires the effective ventilation of the subject to be changed to achieve a change in VCO2. As also mentioned above, this change in effective ventilation may cause unpredictable changes also in cardiac output and EPBF of the subject. By taking the relative variation in cardiac output or EPBF during the analysed sequence of breaths into account, the change in cardiac output or EPBF caused by the change in effective ventilation can be compensated for in the determination of actual cardiac output or EPBF of the ventilated subject.

The relative variation in cardiac output or EPBF may be measured by measuring a quantity that varies in proportion to the cardiac output or EPBF of the ventilated subject during the analysed sequence of breaths.

In one non-limiting embodiment of this disclosure, the step of measuring the relative variation in cardiac output or EPBF involves a step of measuring an arterial pulse pressure signal originating from the ventilated subject, allowing said relative variation to be derived from a pulse pressure signal obtained during the sequence of analysed breaths. The arterial pulse pressure (hereinafter referred to as pulse pressure) signal carries information that is linearly proportional to the cardiac output of the subject as long as the systemic vascular resistance of the subject is constant. The systemic vascular resistance can be assumed to be substantially constant during the relatively short sequence of analysed breaths (typically 4-12 breaths), or changes in the systemic vascular resistance may be compensated. The pulse pressure signal may be any of an invasive arterial pulse pressure signal obtained by means of an artery catheter or the like, or it may be a non-invasive pulse pressure signal obtained by means of a non-invasive pulse pressure device, such as a finger cuff.

An advantage of determining the relative variation in cardiac output or EPBF from a pulse pressure signal is that such signals are often readily available from conventional hemodynamic monitors or cardiac output monitors used to monitor hemodynamic parameters of mechanically ventilated patients.

In accordance with a non-limiting embodiment of this disclosure, the method comprises the steps of determining, from the pulse pressure signal, an uncalibrated measure of the cardiac output or EPBF of the ventilated subject, and using the uncalibrated measure in the determination of the (absolute) cardiac output or EPBF of the ventilated subject. That the measure is uncalibrated means that it varies in proportion to the cardiac output or EPBF of the ventilated subject but is not in itself indicative of an actual or absolute value of cardiac output or EPBF of the subject. This uncalibrated measure, hereinafter referred to as the uncalibrated pulse pressure factor, $PP_{uncal}$, may be determined in any ways known in the art for deriving an uncalibrated or nominal measure of cardiac output or EPBF from a pulse pressure signal. For example, the uncalibrated pulse pressure factor may be determined using uncalibrated pulse contour analysis.

The fact that the pulse pressure signal does not have to be calibrated is advantageous in that the method can be performed without the need for complex calibration techniques, such as the well-known transpulmonary thermodilution technique employed by the PiCCO® plus system from Pulsion Medical Systems, part of Maquet Getinge group, Munich, Germany. Furthermore, uncalibrated pulse pressure measurement devices can be used for measuring the pulse pressure, thus reducing the complexity and the cost of the equipment required for carrying out the proposed method.

The determination of (absolute) cardiac output or EPBF is made in accordance with some embodiments of this disclosure by using a Fick based technique, such as a differential Fick technique.

Thus, according to one aspect of the present disclosure, it is proposed that an uncalibrated method for cardiac output monitoring where the measurement signal is proportional to the cardiac output of the ventilated subject, such as uncalibrated pulse pressure or pulse contour analysis, is combined with a Fick based method for determination of cardiac output or EPBF from respiratory flow and CO2 content, so as to increase the accuracy in the cardiac output or EPBF determination.

Thus, while the above mentioned PiCCO system uses calibrated pulse pressure or pulse contour analysis for determination of cardiac output, the proposed method may employ uncalibrated pulse pressure analysis for measuring relative variations in cardiac output, which variations are used to improve a Fick based method for cardiac output or EPBF determination.

Information derived from the uncalibrated pulse pressure signal can be used in different ways to improve the Fick based determination of cardiac output or EPBF. Also, the type of information derived from the uncalibrated pulse pressure signal and used in the determination of the cardiac output or EPBF of the ventilated subject may differ dependent on the quality of the pulse pressure signal and/or the required accuracy in the cardiac output or EPBF determination.

In some embodiments, the relative variation in cardiac output or EPBF, derived from the measured pulse pressure signal, can be used for post-modification of a cardiac output or EPBF value calculated from the flow and CO2 measurements using a conventional Fick based technique. This means that a first value of cardiac output or EPBF, typically representing a mean value of cardiac output or EPBF during the analysed sequence of breaths, may be calculated from the flow and CO2 measurements using any known Fick based technique, whereupon the first value is modified based on the relative variation of cardiac output or EPBF during the sequence of analysed breaths, as indicated by the measured pulse pressure signal. If, for example, the pulse pressure signal indicates a substantial increase in cardiac output or EPBF during the analysed sequence of breaths, the first value can be slightly increased, e.g. by a fixed amount or a fixed percentage or an amount or a percentage that is determined in dependence of the magnitude of the substantial increase, so as to more accurately reflect the current cardiac output or EPBF of the ventilated subject compared to said first value.

In accordance with some embodiments of this disclosure, however, data derivable from the measured pulse pressure signal are integrated in the Fick based equations that need to be solved in the Fick based determination of cardiac output or EPBF. Instead of assuming constant cardiac output or EPBF for all breaths in the analysed sequence of breaths, data indicative of the relative variation or cardiac output or EPBF, derivable from the pulse pressure signal, may be included in said Fick based equations which are then solved in order to obtain a more accurate cardiac output or EPBF value taking said relative variation into account. For example, the above mentioned uncalibrated pulse pressure factor, $PP_{uncal}$, may be incorporated into the Fick based equations to take relative variation in cardiac output or EPBF of the ventilated subject into account in the cardiac output or EPBF determination. Besides having the effect of improving the accuracy in cardiac output or EPBF determination, inclusion of pulse pressure data indicative of the relative variation in cardiac output or EPBF into the Fick based equations may have the effect of shortening the response time in cardiac output and EPBF determination.

In accordance with some embodiments of this disclosure, the Fick based technique for cardiac output or EPBF determination employs a capnodynamic equation, or rather a system of capnodynamic equations comprising one equation for each breath in the analysed sequence of breaths.

According to one embodiment, the term related to cardiac output or EPBF in each capnodynamic equation is replaced by a term $k*PP_{uncal}$ being a product of a constant 'k' and the above mentioned uncalibrated pulse pressure factor, $PP_{uncal}$, which is directly derivable from the pulse pressure signal. The term $k*PP_{uncal}$ can be said to constitute a variable pulse-pressure dependent measure of cardiac output or EPBF, and the constant 'k' can be said to constitute an unknown calibration constant relating the uncalibrated pulse pressure factor to the actual cardiac output or EPBF of the ventilated subject. Instead of solving the system of capnodynamic equations with respect to cardiac output or EPBF, as made in differential Fick methods according to prior art wherein cardiac output or EPBF is assumed to be constant during the analysed sequence of breaths, the proposed system of capnodynamic equations may be solved with respect to the constant 'k', which is assumed to remain constant during the analysed sequence of breaths (which is true assuming constant cardiovascular resistance). In this way, the term $k*PP_{uncal}$ can be used as an improved measure of (absolute) cardiac output or EPBF, taking variations in cardiac output or EPBF during the analysed sequence of breaths into account.

According to another embodiment, the term related to cardiac output or EPBF in each capnodynamic equation is multiplied by a "weighting factor" representing the relative variation in the uncalibrated pulse pressure factor, $PP_{uncal}$. The system of capnodynamic equations may then be solved with respect to cardiac output or EPBF, in which case the weighting factor serves the purpose of causing the result to depend on the relative variation in $PP_{uncal}$, and thus on relative variations in cardiac output or EPBF during the analysed sequence of breaths.

In certain embodiments of the present disclosure, the method further comprises an alarm step, following the step of determination of cardiac output or EPBF, wherein an alarm is generated if the determined cardiac output or EPBF value falls outside a pre-set range. In this way, clinical personnel may be notified of unexpected deviations in cardiac output or EPBF of the ventilated patient, thereby allowing them to take appropriate measures in dependence of the clinical situations at hand.

The above described method is typically a computer-implemented method that is carried out through execution of a computer program operating on a computer system. Thus, according to another aspect of the present disclosure there is provided a computer program for determination of cardiac output or EPBF of a mechanically ventilated subject. The computer program comprises computer-readable program code segments which, when executed by a processing unit, e.g. a processor of the above mentioned control unit, causes an absolute value of cardiac output or EPBF of a mechanically ventilated subject to be determined from expiratory flow and CO2 measurements obtained during an analysed sequence of breaths, and measurements indicative of a relative variation in cardiac output or EPBF during said analysed sequence of breaths.

The computer program may comprise computer-readable code segments for determining the cardiac output or EPBF of the ventilated subject in accordance with any of the above described principles. The computer program may be stored in a memory device of the above mentioned computer system.

According to yet another aspect of the present disclosure there is provided a ventilation system configured to carry out the above described method for determination of cardiac output or EPBF of a mechanically ventilated subject.

To this end, the system comprises a breathing apparatus, such as a ventilator or an anaesthesia apparatus, for mechanically ventilating the subject. The breathing apparatus is configured to introduce a change in the effective ventilation of the ventilated subject, e.g. by changing the duration of breaths delivered to the subject. The system further comprises a flow sensor and a CO2 sensor for measuring expiratory flow and CO2 during a sequence of analysed breath during which the effective ventilation of the subject varies, and a control unit, e.g. a control computer, configured to determine the cardiac output or EPBF of the subject using the flow and CO2 measurements obtained by the flow sensor and the CO2 sensor during the analysed sequence of breaths. Furthermore, the system comprises a device for measuring a relative variation in the cardiac output or EPBF of the ventilated subject during the analysed sequence of breaths, whereby the control unit is configured to use also the relative variation in the cardiac output or EPBF determination.

The device for measuring the relative variation in cardiac output or EPBF is, in accordance with certain embodiments of this disclosure, a pulse pressure device configured to measure a pulse pressure signal indicative of the relative variation in cardiac output or EPBF, whereby the control unit may be configured to use pulse pressure data derived from the pulse pressure signal in the determination of cardiac output or EPBF.

The device for measuring the relative variation in cardiac output or EPBF may constitute an integral part of the breathing apparatus or be a separate device not forming part of the breathing apparatus. Likewise, the control unit that determines the cardiac output or EPBF of the ventilated subject using both the flow and CO2 measurements and the relative variations in cardiac output or EPBF may be a control unit of the breathing apparatus or a control unit of an external monitoring system for monitoring parameters related to the ventilated subject and/or the operation of the breathing apparatus.

In one embodiment, the device for measuring a relative variation in the cardiac output or EPBF of the ventilated subject is an external device not forming part of the breathing apparatus, such as a haemodynamic monitor or cardiac output monitor, whereas the control unit is an internal control unit of the breathing apparatus which is configured to receive measurements of the relative variation in cardiac output or EPBF from the external device. In accordance with some embodiments of this disclosure, said external device is a device that is configured for uncalibrated pulse pressure or pulse contour analysis, capable of transmitting uncalibrated pulse pressure data indicative of the relative variation in cardiac output or EPBF to the breathing apparatus, for further processing by the control unit of the breathing apparatus in accordance with any of the principles described above.

According to yet another aspect of the present disclosure there is provided a ventilation system comprising a computer associated with the above described computer program, wherein the computer program directs the computer to determine cardiac output or EPBF of the mechanically ventilated subject from the expiratory flow and CO2 measurements obtained during the analysed sequence of breaths, and from the measurements indicative of the relative variation in cardiac output or EPBF of the subject during said analysed sequence of breaths. In accordance with certain embodiments of this disclosure, the computer may constitute or form part of the control unit of the breathing apparatus.

More advantageous aspects of the proposed method, computer program and system will be described in the detailed description of embodiments following hereinafter.

BRIEF DESCRIPTION OF THE DRAWINGS

Embodiments of this disclosure will become more fully understood from the detailed description provided hereinafter and the accompanying drawings which are given by way of illustration only.

In the different drawings, same reference numerals correspond to the same element.

DETAILED DESCRIPTION

Figure 1:
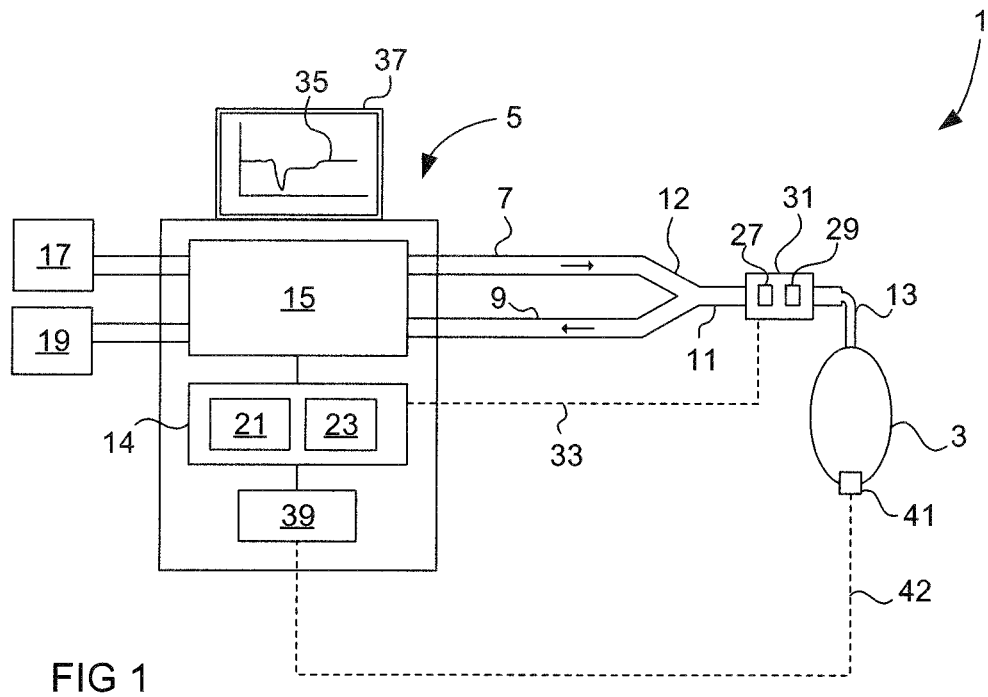
FIG. 1 illustrates a system for determination of cardiac output or EPBF of a mechanically ventilated subject, according to a first embodiment of the present disclosure.

FIG. 1 illustrates a system 1 for determination of cardiac output or EPBF of a mechanically ventilated subject 3, hereinafter sometimes referred to as the patient, according to a first non-limiting, illustrating embodiment of the present disclosure.

The system 1 comprises a breathing apparatus 5, such as a ventilator or an anaesthesia apparatus, for providing ventilatory treatment to the patient 3. The breathing apparatus 5 is connected to the patient 3 via an inspiratory line 7 for supplying breathing gas to the patient 3, and an expiratory line 9 for conveying expiration gas away from the patient 3. The inspiratory line 7 and the expiratory line 9 are connected to a common line 11, via a so called Y-piece 12, which common line is connected to the patient 3 via a patient connector 13, such as a facemask or an endotracheal tube.

The breathing apparatus 5 further comprises a control unit 14 for controlling the ventilation of the patient 3 based on preset parameters and/or measurements obtained by various sensors of the breathing apparatus. The control unit 14 controls the ventilation of the patient 3 by controlling a pneumatic unit 15 of the breathing apparatus 5, which pneumatic unit 15 is connected at one hand to one or more gas sources 17, 19 and at the other hand to the inspiratory line 7 for regulating a flow and/or pressure of breathing gas delivered to the patient 3. To this end, the pneumatic unit 15 may comprise various gas mixing and regulating means well known in the art of ventilation, such as gas mixing chambers, controllable gas mixing valves and one or more controllable inspiration valves.

The control unit 14 comprises a processing unit 21 and a non-volatile memory 23 storing a computer program for determining the cardiac output or EPBF of the patient 3 according to the principles described herein. Unless stated otherwise, actions and method steps described hereinafter are performed by, or caused by, the control unit 14 of the breathing apparatus 5 upon execution by the processing unit 21 of different code segments of the computer program stored in the memory 23.

The breathing apparatus 5 further comprises at least one flow sensor 27 for measuring at least an expiratory flow of expiration gas exhaled by the patient 3, and at least one $CO_2$ sensor 29 for measuring the $CO_2$ content of at least the expiration gas exhaled by the patient. The control unit 14 is configured to determine the cardiac output or EPBF of the patient 3 at least partly based on flow and $CO_2$ measurements obtained by the flow and $CO_2$ sensor, respectively, as will be described in more detail below. Preferably, the flow and $CO_2$ sensors 27, 29 are configured to measure also inspiratory flow and $CO_2$ content.

In the illustrated embodiment, the flow sensor 27 and the $CO_2$ sensor 29 form parts of a capnograph 31 configured for volumetric capnography measurements. The capnograph 31 is arranged in the proximity of the airway opening of the patient 3, namely, in the common line 11 of the breathing circuit in which it is exposed to all gas exhaled and inhaled by the patient 3. The capnograph 31 is connected to the ventilator 5 via a wired or wireless connection 33, and configured to communicate the result of the flow and $CO_2$ measurements to the ventilator for further processing by the processing unit 21 of the ventilator. The ventilator 5 may be configured to generate a volumetric capnogram 35 from the flow and $CO_2$ measurements received from the capnograph 31, and, additionally, to display the volumetric capnogram 35 on a display 37 of the ventilator.

The system 1 further comprises a device 39 for measuring a relative variation in cardiac output or EPBF of the patient 3. Preferably, the device 39 is a pulse pressure device or analyser for deriving pulse pressure data indicative of relative variations in cardiac output or EPBF from the pulse pressure (i.e. arterial pressure) of the patient 3. To this end, the system further comprises a pulse pressure signal sensor 41 configured to detect a signal indicative of the pulse pressure of the patient 3. The pulse pressure signal sensor 41 may be a non-invasive pulse pressure sensor, such as a finger cuff for pulse pressure measurement, or an invasive pulse pressure sensor for invasive pulse pressure measurement, such as an artery catheter (arterial line) for pulse pressure measurement. In one embodiment, the pulse pressure sensor 41 is an artery catheter configured for insertion into the axillary, brachial or femoral artery of the patient 3.

In the illustrated embodiment, the pulse pressure device 39 is integrated in the breathing apparatus 5 and connected to the pulse pressure sensor 41 via a signalling line 42. The pulse pressure device 39 is further connected to the control unit 14 of the breathing apparatus 5, and configured to provide the control unit with pulse pressure data derived from the pulse pressure signal obtained by the sensor 41, for subsequent use by the control unit 14 in determination of cardiac output or EPBF of the patient 3.

The control unit 14 is configured to determine the cardiac output or EPBF of the patient 3 from the flow and $CO_2$ measurements obtained by the flow and $CO_2$ sensors 27, 29 using a non-invasive Fick method, which is adapted or supplemented to take relative variations in cardiac output or EPBF into account by using the pulse pressure measurements obtained by the pulse pressure sensor 41, as will be described in more detail below.

Fick based determination of cardiac output or EPBF typically requires the level of expired $CO_2$ to change with at least 0.2% and preferably around 0.5% or more during the analysed sequence of breaths. To this end, the control unit 14 is configured to introduce a change in the effective ventilation of the patient 3 by changing one or more breathing apparatus settings controlling the ventilation of the patient 3, and to determine the cardiac output or EPBF of the patient based on the flow and $CO_2$ measurements obtained during an analysed sequence of breaths during which the change in effective ventilation occurs.

As in most Fick based methods for cardiac output determination, the analysed sequence of breaths may comprise any number of breaths but typically comprises 4 to 20 breaths, and preferably 4 to 12 breaths. The analysed sequence of breaths comprises at least one phase of increased ventilation and at least one phase of decreased ventilation, wherein each phase of increased and decreased ventilation comprises at least one breath, typically at least two breaths, and preferably two to six breaths. The transition from the phase of increased ventilation to the phase of decreased ventilation, and vice versa, is effectuated by the change in effective ventilation of the patient 3. The change in effective ventilation may be caused by the control unit 14 in any manner known in the art, e.g. by changing the duration and/or the tidal volume of the breaths delivered to the patient by the breathing apparatus.

Preferably, in order to determine cardiac output or EPBF continuously, the breathing apparatus 5 is configured to ventilate the patient 3 using a cyclic ventilation pattern comprising alternating phases of decreased and increased ventilation, wherein each phase of decreased ventilation is immediately followed by a phase on increased ventilation, and vice versa. Preferably, but not necessarily, the number of breaths in each cycle of the cyclic ventilation pattern corresponds to the number of breaths in the analysed sequence of breaths.

The pulse pressure data derived from the pulse pressure signal obtained by the sensor 41 and used by the control unit 14 in the determination of cardiac output or EPBF of the patient 3 may be any pulse pressure data indicative of the relative variation of the cardiac output or EPBF of the patient 3. Preferably, the pulse pressure data is indicative of the variation of a quantity that is directly proportional to the cardiac output or EPBF of the patient. An advantage of the proposed concept for cardiac output or EPBF determination is that the pulse pressure data can be derived from an uncalibrated pressure pulse signal or, in other words, that the pulse pressure data can be derived from the pulse pressure signal using an uncalibrated method for pulse pressure or pulse contour analysis.

Pulse contour analysis is an indirect method for cardiac output estimation, the original concept of which was first described by Otto Frank in 1899 as the classic Windkessel model in "die Grundform des Arteriellen Pulses", Zeitschrift for Biologie 37: 483-526 (1899). Most pulse contour methods used today are derived from the Windkessel model, including e.g. the Wesseling's cZ method, the Modelflow method, the Hemac pulse contour method, the PulseCO cardiac output method, as well as the above mentioned PiCCO method, all of which are described in further detail in de Wilde et al., An evaluation of cardiac output by five arterial pulse contour techniques during cardiac surgery, Anaesthesia, 2007, 62, pages 760-768.

In order to determine an absolute value of cardiac output using any of these methods, a nominal or uncalibrated measure of cardiac output derived from the pulse contour analysis must be calibrated using an independent method for cardiac output determination. Most often, an independent dilution technique, such as a thermodilution or lithium dilution based method, is used to calibrate the uncalibrated measure of cardiac output to obtain the absolute cardiac output value.

The uncalibrated cardiac output measure may be derived from the pulse pressure signal in different ways, but is typically derived from the area under the systolic portion of the arterial pulse pressure signal. Dividing the area under the systolic portion of the pulse pressure signal by aortic impedance provides a measure of stroke volume. Much simplified, an uncalibrated measure of cardiac output can then be calculated as the so determined measure of stroke volume times the heart rate of the patient, typically by first compensating in various ways for pressure dependent non-linear changes in cross sectional area of the aorta, pressure reflections from the periphery, the age of the patient, etc.

The pulse pressure data used in the calculations of cardiac output or EPBF according to the principles of the present disclosure may comprise an uncalibrated pulse pressure factor, herein referred to as $PP_{uncal}$, which is calculated according to any known principle for calculation of an uncalibrated measure of cardiac output using pulse contour analysis. For example, $PP_{uncal}$, may correspond to the uncalibrated measure of cardiac output calculated in accordance with the above described principles.

Thus, the proposed method may use an uncalibrated pulse pressure factor, $PP_{uncal}$, that is derived from the pulse pressure signal and preferably from the area under the systolic portion of the pulse pressure signal together with flow and CO2 measurements obtained during an analysed sequence of breaths in a Fick based method for cardiac output or EPBF determination, to take relative variations in cardiac output or EPBF during the analysed sequence of breath, as reflected by the uncalibrated pulse pressure factor, into account in the determination.

In some embodiments, the control unit 14 may be configured to determine a first and approximate cardiac output or EPBF value from the flow and CO2 measurements obtained during the analysed sequence of breaths using any known Fick based technique, such as any of the techniques described in WO 2006/119546, U.S. Pat. No. 7,135,001, WO2013/141766, EP2799008 or PCT/SE2015/051357, and to adjust the approximate cardiac output or EPBF value based on any relative variation in cardiac output or EPBF during the analysed sequence of breaths, as indicated by uncalibrated pulse pressure factor, $PP_{uncal}$. For example, the control unit 14 may be configured to determine a second and actual cardiac output or EPBF value by increasing or decreasing the approximate cardiac output or EPBF value by an amount or percentage that may be preset or selected in dependence of the magnitude of the relative variation in cardiac output or EPBF, as indicated by the pulse pressure signal measured during the analysed sequence of breaths. This means that the method may involve calculation of a variable absolute value of, e.g., EPBF according to the principle:

$$EPBF_{variable} = EPBF_{Fick} \cdot f(PP_{uncal}) \qquad \text{Eq. 3}$$

where $EPBF_{variable}$ hence is an absolute value of EPBF calculated according to the principles of the present disclosure, $EPBF_{Fick}$ is an EPBF value calculated using any known Fick technique assuming constant EPBF during the analysed sequence of breaths, and $f(PP_{uncal})$ is any suitable function of an uncalibrated pulse pressure factor $PP_{uncal}$ indicative of relative variations in cardiac output or EPBF during the analysed sequence of breaths.

In another embodiment, the control unit 14 is configured to determine the cardiac output or EPBF of the patient 3 using a Fick based method employing a capnodynamic equation in which the term related to cardiac output or EPBF is replaced by a term that is a product of a constant, k, and the pulse pressure factor $PP_{uncal}$ derived from the pulse pressure measurements, which factor varies in proportion to the cardiac output or EPBF of the patient 3.

For each breath, n, in the analysed sequence of breath, the following capnodynamic equation applies:

$$ELV \cdot (F_A CO2^n - F_A CO2^{n-1}) = \Delta t^n \cdot EPBF^n \cdot (CvCO2 - CaCO2^n) - VTCO2^n \qquad \text{Eq. 4}$$

where ELV is the effective lung volume of the patient during the analysed sequence of breath (assumed to be constant), $F_A CO2^n - F_A CO2^{n-1}$ ($\Delta F_A CO2$) is the change in volume fraction of alveolar CO2 of the patient since the last breath, $\Delta t^n$ is the duration of the breath, $EPBF^n$ is the effective pulmonary blood flow of the patient during the breath, $CvCO_2$ is the carbon dioxide content of venous blood of the patient during the analysed sequence of breaths (assumed to be constant), $CaCO_2$ is the carbon dioxide content of arterial blood of the patient during the breath, and $VTCO_2$ is the tidal volume elimination of CO2 of the patient during the breath, i.e. the volume of CO2 eliminated by the patient during the breath.

This equation is similar to equations used for determination of cardiac output or EPBF according to prior art (cf. equation 1 in WO2013/141766), with the difference that EPBF is not treated as being constant during the analysed sequence of breaths but rather as being allowed to vary between breaths of the analysed sequence.

The control unit 14 may be configured to use a modified version of equation 4 wherein, for each breath in the analysed sequence of breaths, EPBF is expressed in terms of $PP_{uncal}$, determined by the pulse pressure device 39 from the pulse pressure signal obtained by the sensor 41, according to:

$$ELV \cdot (F_ACO2^n - F_ACO2^{n-1}) = \Delta t^n \cdot k \cdot PP_{uncal}^n \cdot (CvCO2 - CaCO2^n) - VTCO2^n \quad \text{Eq. 5A}$$

In equation 5A, $EPBF^n$ in equation 4 has been replaced by a term $k \cdot PP_{uncal}^n$ which is a product of a constant 'k' and the pulse pressure factor $PP_{uncal}$. The term $k \cdot PP_{uncal}$ can be said to constitute a variable pulse-pressure dependent measure of cardiac output or EPBF, and the constant 'k' can be said to constitute a calibration constant relating relative variations in the uncalibrated pulse pressure factor $PP_{uncal}$ to actual variations in cardiac output or EPBF of the patient 3.

$PP_{uncal}$ is thus a measured quantity that may vary between consecutive breaths, and the constant 'k' is determined by solving the capnodynamic equation 5 using measurement values of $F_ACO2$, $CaCO2$ and $VTCO2$, directly obtainable from the flow and CO2 measurements obtained by the flow and CO2 sensors 27, 29. Preferably, 'k' is determined in accordance with the principles described in WO2013/141766, which means that the parameter triplet {ELV, k, CvCO2} is determined by solving or rather finding an approximate solution to an overdetermined system of equations comprising one capnodynamic equation corresponding to equation 5 for each breath in the analysed sequence of breaths, e.g., by using the method of least squares.

Once the value for the constant 'k' has been calculated, a current value of the variable EPBF of the patient 3 may be determined in accordance with the principles of the present disclosure as:

$$EPBF_{variable} = k \cdot PP_{uncal}^N \quad \text{Eq. 6A}$$

where $PP_{uncal}^N$ is the pulse pressure factor determined for the last breath, N, in the analysed sequence of breath.

In other embodiments, the control unit 14 may be configured to use the following modified version of equation 4 in the determination of a current value of the variable EPBF of the patient 3:

$$ELV \cdot (F_ACO2^n - F_ACO2^{n-1}) = \quad \text{Eq. 5B}$$
$$\Delta t^n \cdot \overline{EPBF} \cdot \frac{PP_{uncal}^n}{\overline{PP}_{uncal}} \cdot (CvCO2 - CaCO2^n) - VTCO2^n$$

where $\overline{EPBF}$ is a mean value of EPBF during the analysed sequence of breaths and $\overline{PP}_{uncal}$ is the mean value of $PP_{uncal}$ during the analysed sequence of breaths. The factor $PP_{uncal}^n / \overline{PP}_{uncal}$ is a measure of the relative variation in $PP_{uncal}$ for each breath n, which, when solving equation 5B with respect to $\overline{EPBF}$, serves to take the relative variation in cardiac output or $\overline{EPBF}$ during the analysed sequence of breaths into account in the determination of $\overline{EPBF}$. In accordance with the above described principles for determination of the constant 'k', EPBF may be determined by solving equation 5B using the method described in WO2013/141766, which means that the parameter triplet {ELV, $\overline{EPBF}$, CvCO2} is determined by solving an overdetermined system of equations comprising one capnodynamic equation corresponding to equation 5B for each breath in the analysed sequence of breaths.

The control unit 14 of the breathing apparatus 1 may be configured to determine the value of the variable EPBF of the patient 3 to correspond to the thus determined mean value, $\overline{EPBF}$:

$$EPBF_{variable} = \overline{EPBF} \quad \text{Eq. 6B}$$

Although the variable EPBF value, $EPBF_{variable}$, determined in accordance with equation 6B represents a mean value of EPBF during the analysed sequence of breaths, it should be noted that this is a more accurate mean value than those determined using conventional Fick techniques in which EPBF is assumed to be constant during the analysed sequence of breaths. To some extent, the factor $PP_{uncal}^n / \overline{PP}_{uncal}$ in equation 5B may be regarded as a weighting factor for EPBF, serving to take relative variations in cardiac output or EPBF into account in the EPBF determination.

Furthermore, although equations 5A and 5B are similar in nature, equation 5B may be advantageous in that a measure of the variable EPBF of the patient 3 is obtained as a direct result of solving the system of equations. Yet further, while use of equation 5A involves determination of a calibration constant 'k' to be multiplied by the uncalibrated pulse pressure factor $PP_{uncal}$, equation 5B clearly illustrates the advantage of the proposed method of not requiring calibration of the pulse pressure data used in the cardiac output or EPBF determination.

As well known in the art, cardiac output relates to EPBF according to the formula:

$$CO \cdot (1 - f_s) = EPBF \quad \text{Eq. 7}$$

where CO is cardiac output and $f_s$ is the pulmonary shunt fraction, meaning that cardiac output is directly proportional to EPBF in case of constant shunt. For the sake of completeness, it should be mentioned that in the above calculations, the shunt fraction is assumed to be constant during the analysed sequence of breaths. If so, the pulse pressure factor $PP_{uncal}$ will be directly proportional to both cardiac output and EPBF, and the above calculations will provide an accurate absolute value of the variable EPBF, $EPBF_{variable}$, of the patient 3. If, however, the shunt fraction varies during the analysed sequence of breaths, the above equations may be modified to take such variations into account. If desired, once the actual value of EPBF, $EPBF_{variable}$, has been determined in accordance with equation 3, 6A or 6B, an actual value of cardiac output can be determined from equation 7 by employing any method known in the art for determination of the shunt fraction $f_s$.

Figure 2:
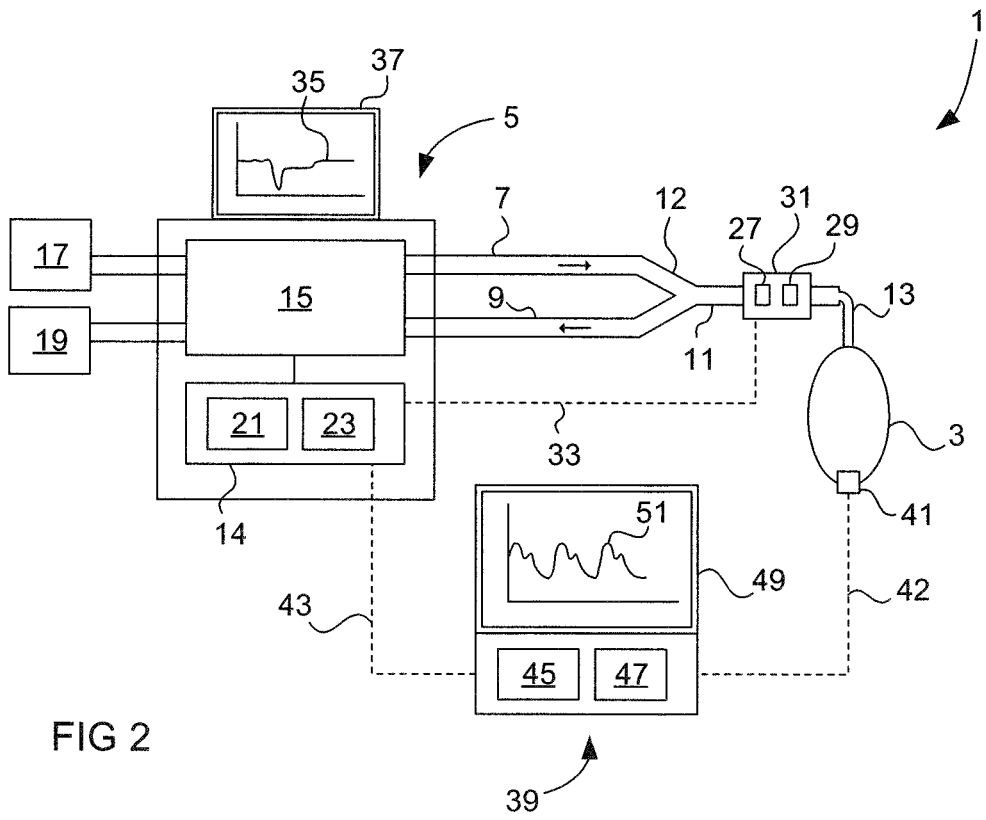
FIG. 2 illustrates a system for determination of cardiac output or EPBF of a mechanically ventilated subject, according to a second embodiment of the present disclosure.

FIG. 2 illustrates a system 1 for determination of cardiac output or EPBF of a mechanically ventilated patient 3, according to a second embodiment of the present disclosure.

The system 1 is identical to the system illustrated in FIG. 1, with the exception that the pulse pressure device 39 for obtaining and providing to the control unit 15 the pulse pressure data indicative of the relative variation in cardiac output or EPBF of the patient 3 is not integrated in the breathing apparatus 5. Instead, the pulse pressure device 39 is a separate stand-alone device which is communicatively connected to the breathing apparatus 5 via a wired or wireless signalling line 43, and configured to transmit pulse pressure data derived from the pulse pressure signal to the control unit 14 via the signalling line, for subsequent use of the pulse pressure data by the control unit 14 in the determination of cardiac output or EPBF of the patient 3, as described above with reference to FIG. 1.

The stand-alone pulse pressure device 39 may be a hemodynamic monitor or cardiac output monitor. For example, the stand-alone pulse pressure device 39 may be a conventional hemodynamic monitor of the type employed by the PiCCO® plus system from Pulsion Medical Systems. As mentioned above, the nominal or uncalibrated measure of cardiac output, often referred to as PCCO, provided by the PiCCO monitor and obtained through pulse contour analysis, is normally calibrated using transpulmonary thermodilution technique. If the PiCCO system is not calibrated, the PCCO values delivered by the PiCCO monitor will represent uncalibrated measures of the cardiac output of the patient 3, which measures are still indicative of the relative variation in cardiac output or EPBF of the patient 3 and so can be used by the control unit 14 as the uncalibrated pulse pressure factor, $PP_{uncal}$, in the determination of absolute cardiac output or EPBF, as described above.

The stand-alone pulse pressure device 39 is seen to comprise a processing unit 45 and a memory 47 storing a computer program for calculation of an uncalibrated measure of cardiac output or EPBF of the patient 3 based on a pulse pressure signal obtained by the pulse pressure sensor 41, connected to the pulse pressure device 39 via the signalling line 42. The pulse pressure device 39 is further seen to include a display unit 49 for the display of information related to the pulse pressure signal, the cardiac output and/or the EPBF of the patient 3. In the illustrated scenario, a signal curve 51 representing the pulse pressure signal detected by the pulse pressure sensor 41 is displayed on the display unit 49.

Figure 3:
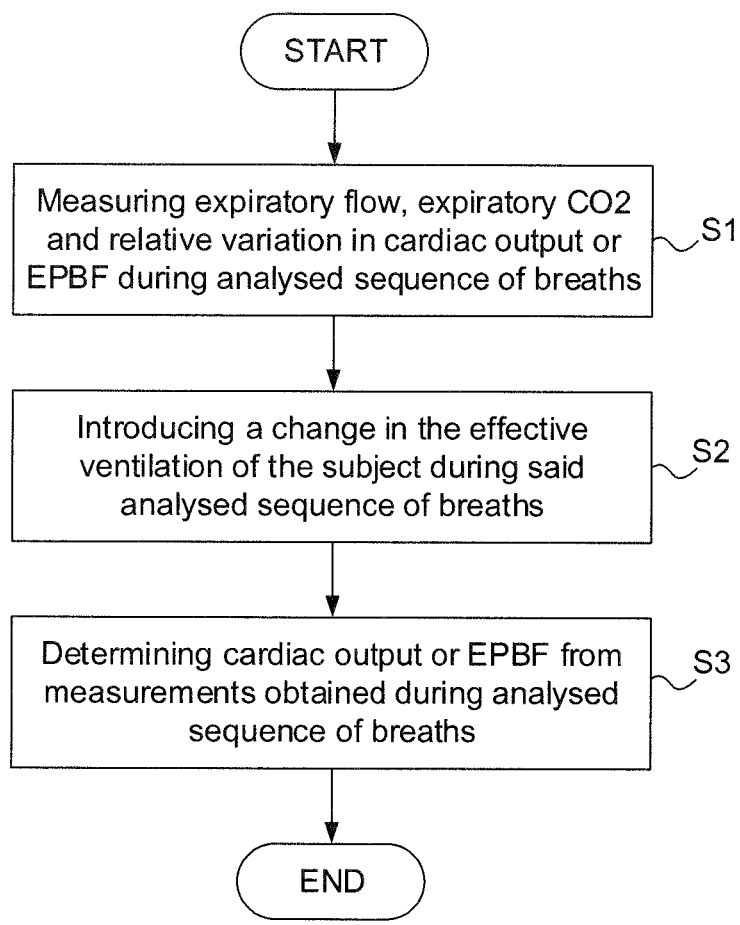
FIG. 3 is a flow chart illustrating a method for determination of cardiac output or EPBF of a mechanically ventilated subject, according to a second embodiment of the present disclosure.

FIG. 3 is a flow chart illustrating a method for determination of cardiac output or EPBF of a mechanically ventilated subject, according to an embodiment of the present disclosure.

In a first step, S1, expiratory flow and CO2 as well as relative variations in cardiac output or EPBF of the subject are measured during an analysed sequence of breaths. As mentioned above, expiratory flow and CO2 may be measured using a capnograph, or the like, such as the capnograph 31 schematically illustrated in FIGS. 1 and 2, devised to measure flow and CO2 content of expiration gases exhaled by the subject. Relative variations in cardiac output or EPBF may be measured by any device capable of measuring a quantity that varies in proportion with the cardiac output or EPBF of the patient, such as the pulse pressure device 39 schematically illustrated in FIGS. 1 and 2.

In a second step, S2, a change in the effective ventilation of the subject is introduced in order to cause a change in the level of expired CO2, thereby allowing the cardiac output or EPBF of the ventilated subject to be determined from the expiratory flow and CO2 measurements using a Fick based method for cardiac output or EPBF determination. The change in effective ventilation is introduced during the taking of such measurements such that the level of expired CO2 varies during the analysed sequence of breaths. This means that measurements are obtained both prior to and after a change in the level of expired CO2, caused by the change in effective ventilation.

In a third step, S3, the cardiac output or EPBF of the ventilated subject is determined from the expiratory flow and CO2 measurements and the measurements of the relative variation in cardiac output or EPBF of the subject, obtained during the analysed sequence of breaths. For example, a current actual value of cardiac output or EPBF of the ventilated subject can be determined from the measurements using any of equation 3, 6A or 6B.

In a subsequent step (not shown), the cardiac output or EPBF value determined in step S3 may be compared with one or more threshold values, defining a recommended and pre-set range for cardiac output or EPBF, whereupon an alarm signal may be generated in response to the comparison should the determined cardiac output or EPBF value fall outside the recommended range.

The method is typically computer-implemented, meaning that it is performed through execution of a computer program. As mentioned above, the various method steps are typically performed by, or caused by, the control unit 14 of the breathing apparatus 5 upon execution by the processing unit 21 of different code segments of the computer program, which may be stored in the hardware memory device 23.

The invention claimed is:

1. A method for determining a cardiac output or an Effective Pulmonary Blood Flow ("EPBF") of a mechanically ventilated subject, the method comprising:
   introducing a change in an effective ventilation provided by a breathing apparatus to the subject, wherein the change of ventilation is caused by a control unit of the breathing apparatus by changing one or more settings of the breathing apparatus;
   measuring expiratory flow and $CO_2$ content of expiration gas exhaled by the subject during a sequence of respiratory cycles during which the effective ventilation of the subject varies, wherein the expiratory flow is measured by at least one flow sensor of the breathing apparatus and the expiratory $CO_2$ content is measured by at least one $CO_2$ sensor of the breathing apparatus;
   measuring a relative variation in cardiac output or EPBF during the sequence of respiratory cycles, wherein the relative variation is derived from a pulse pressure signal obtained by a pulse pressure device during the sequence of respiratory cycles;
   determining the cardiac output or the EPBF of the subject by the control unit based on the measured expiratory flow received by the control unit from the at least one flow sensor, the measured $CO_2$ content received by the control unit from the at least one $CO_2$ sensor, and the relative variation in cardiac output or EPBF, and
   continuously monitoring the cardiac output or the EPBF of the subject with the control unit.

2. The method of claim 1, further comprising determining by the control unit the cardiac output or the EPBF using an uncalibrated pulse pressure factor ("$PP_{uncal}$") that varies in proportion to the cardiac output or EPBF of the ventilated subject, which uncalibrated pulse pressure factor is derived from the pulse pressure signal.

3. The method of claim 1, wherein the determination of the cardiac output or EPBF of the ventilated subject is made using a Fick based technique.

4. The method of claim 3, wherein the Fick based technique employs a capnodynamic equation or a system of capnodynamic equations in which the uncalibrated pulse pressure factor is incorporated to take the relative variation in cardiac output or EPBF of the subject into account in the cardiac output or the EPBF determination.

5. The method of claim 1, further comprising a step of generating an alarm if the determined cardiac output or EPBF value falls outside a pre-set range of values for the cardiac output or the EPBF, respectively.

6. A non-transitory, computer-readable data storage medium with an executable program stored thereon, wherein the program instructs a processing unit to perform operations for controlling a breathing apparatus and determining a cardiac output or an Effective Pulmonary Blood Flow ("EPBF") of a mechanically ventilated subject, when executed by the processing unit, the operations comprising steps to:

introduce a change in an effective ventilation provided by a breathing apparatus to the subject by changing one or more settings of the breathing apparatus;

receive measurements of an expiratory flow of expiration gas exhaled by the subject from at least one flow sensor and measurements of an expiratory $CO_2$ content of the expiration gas from at least one $CO_2$ sensor, both of which are obtained during a sequence of respiratory cycles during which the effective ventilation of the subject varies;

derive a relative variation in cardiac output or EPBF during the sequence of respiratory cycles from a pulse pressure signal obtained by a pulse pressure device during the sequence of respiratory cycles;

determine the cardiac output or the EPBF of the subject based on the received measurements of expiratory flow, the received measurements of $CO_2$ content of expiration gas, and the relative variation in cardiac output or EPBF, and continuously monitor the cardiac output or the EPBF of the subject with the control unit.

7. A system configured to control delivery of mechanical ventilation to a subject and to monitor a cardiac output or an Effective Pulmonary Blood Flow ("EPBF") of the mechanically ventilated subject, comprising:

a breathing apparatus configured to deliver the mechanical ventilation to the subject;

a control unit configured to introduce a change in the effective ventilation provided by the breathing apparatus to the subject by changing one or more settings of the breathing apparatus;

a flow sensor configured to measure an expiratory flow of expiration gas exhaled by the subject during a sequence of respiratory cycles during which an effective ventilation of the subject varies, and to provide the expiratory flow measurements to the control unit;

a $CO_2$ sensor configured to measure an expiratory $CO_2$ content of the expiration gas during the sequence of respiratory cycles, and to provide the expiratory $CO_2$ measurements to the control unit;

the control unit being configured to:

derive a relative variation in cardiac output or EPBF during the sequence of respiratory cycles from a pulse pressure signal obtained by a pulse pressure device during the sequence of respiratory cycles;

determine the cardiac output or the EPBF of the subject based on the expiratory flow measurements provided by the flow sensor, the expiratory $CO_2$ measurements provided by the $CO_2$ sensor, and the relative variation in cardiac output or EPBF, and continuously monitor the cardiac output or the EPBF of the subject.

8. The system of claim 7, wherein the pulse pressure device is configured to measure a pulse pressure signal indicative of the relative variation of cardiac output or EPBF during the sequence of respiratory cycles.

9. The system of claim 7, wherein the pulse pressure device is an external device not forming part of the breathing apparatus, the control unit being an internal control unit of the breathing apparatus configured to receive measurements of the pulse pressure signal from the external pulse pressure device.

10. The system of claim 7, wherein the control unit is configured to determine the cardiac output or the EPBF using an uncalibrated pulse pressure factor ("$PP_{uncal}$") that varies in proportion to the cardiac output or the EPBF of the ventilated subject, wherein the uncalibrated pulse pressure factor is derived from the pulse pressure signal.

11. The system of claim 10, wherein the control unit is configured to use a Fick based technique employing a capnodynamic equation or a system of capnodynamic equations in which the uncalibrated pulse pressure factor is incorporated to take the relative variation in cardiac output or EPBF of the subject into account in the cardiac output or EPBF determination.

12. The system of claim 7 wherein the control unit is configured to determine the cardiac output or the EPBF of the ventilated subject using a Fick based technique.

13. The system of claim 7, wherein the pulse pressure device that measures the pulse pressure signal is at least partly integrated in the breathing apparatus.

* * * * *